United States Patent [19]

DeLuca et al.

[11] 4,297,289
[45] Oct. 27, 1981

[54] VITAMIN D COMPOUNDS ISOTOPICALLY SUBSTITUTED AT CARBON 6 AND PROCESS FOR THEIR PREPARATION

[75] Inventors: Hector F. DeLuca; Heinrich K. Schnoes, both of Madison; Herbert E. Paaren, Verona; Mary A. Fivizzani, Madison, all of Wis.

[73] Assignee: Wisconsin Alumni Research Foundation, Madison, Wis.

[21] Appl. No.: 169,567

[22] Filed: Jul. 17, 1980

[51] Int. Cl.³ .............................................. C07J 9/00
[52] U.S. Cl. ................................................ 260/397.2
[58] Field of Search ..................................... 260/397.2

[56] References Cited

U.S. PATENT DOCUMENTS 4,195,027  3/1980  DeLuca et al. ................. 260/397.2
4,224,231  9/1980  DeLuca et al. ................. 260/397.2

Primary Examiner—Elbert L. Roberts
Attorney, Agent, or Firm—Howard W. Bremer

[57] ABSTRACT

A method for isotopically labeling carbon-6 of vitamin D and 5,6-trans-vitamin D compounds which comprises reducing the corresponding 6-oxo-cyclovitamin with a tritio- or deutero-borohydride and subjecting the reduction product to acid-catalyzed solvolysis.

The 6-labeled compounds find application in the elucidation of vitamin D metabolism and function and in vitamin metabolite analyses.

28 Claims, No Drawings

VITAMIN D COMPOUNDS ISOTOPICALLY SUBSTITUTED AT CARBON 6 AND PROCESS FOR THEIR PREPARATION

The invention described herein was made in the course of work under a grant or award from the Department of Health and Human Services.

This invention relates to isotopically labeled vitamin D compounds.

More specifically, this invention relates to a method for the preparation of vitamin D and its metabolites and analogs labeled with deuterium or tritium of carbon 6 of the molecule, and to novel compounds which are key intermediates in this labeling process.

Vitamin D is an important agent for the control of the calcium and phosphate balance in an organism, and the regulation of bone formation. It is also well established that these biological functions of vitamin D require metabolism to hydroxylated metabolites which are the biologically active agents. For example, vitamin $D_3$ is metabolized in the animal and human to 25-hydroxyvitamin $D_3$ and then to $1\alpha,25$-dihydroxyvitamin $D_3$, and it is the latter compound, in particular, that is responsible for the stimulation of calcium transport in intestine and the liberation of calcium from bone mineral. Other metabolites of vitamin $D_3$ are also known, although their precise in vivo functions are not entirely clear. Similarly, an analogous series of vitamin $D_2$ metabolites has been characterized (see for example, DeLuca et al. in "Topics in Current Chemistry," Vol. 83, Biochemistry, pp. 1–66, Springer-Verlag, New York, 1979).

For the establishment of the above-mentioned facts the availability of isotopically labeled vitamin D compounds was of crucial importance. Radiolabeled vitamin D compounds have been essential for the elucidation of vitamin D metabolism and function (for example, DeLuca and Schnoes, Ann. Rev. Biochem. 45, 631, 1976) and have been used widely also in assays of vitamin D metabolites [e.g. Belsey et al. J. Clin. Endocrinol. Meta. 33, 992, (1971); Haddad et al. J. Clin. Endocrinol. Metab. 43, 86, (1976); Edelstein et al. Clin. Sci. Mol. Med. 46, 231 (1974); Eisman et al. Anal. Biochem. 80, 298 (1977); Brumbaugh et al. Science 183, 1089 (1974); Eisman et al. Arch. Biochem. Biophys. 176, 235 (1976); Shepard et al. Biochem. J. 182, 55, (1979)]. Vitamin D compounds labeled with stable isotopes (e.g. $^2H$) are also useful for metabolite analysis in blood and tissues especially by mass spectrometric methods, as shown for example by Bjorkhem and Holmberg, Clin. Chim. Acta 68, 215 (1976), and Bjorkhem et al. Clin. Chem. 25, 584 (1979).

This widespread need for isotopically labeled viatmin D compounds has stimulated considerable interest in methods for their preparations and a number of effective isotope syntheses yielding specific vitamin D products have been devised e.g. Neville and DeLuca, Biochemistry 5, 2201 (1966); DeLuca et al. Arch. Biochem. Biophys. 124, 122 (1968); Suda et al, Anal. Biochem. 43, 139 (1971); Bell and Scott, J. Label. Compds. 9, 339 (1973); Holick, et al. J. Biol. Chem. 251, 1020 (1976); Jones et al. Biochemistry 14, 1250 (1975); Yamada et al. Anal. Biochem. 85, 37 (1978); Muccino et al. Steroids 31, 645 (1978); and Napoli, et al. Anal. Biochem. 96, 481 (1979).

Most of these available methods, based on isotopic labeling of suitable steroids followed by multistep conversions to the vitamin D compound, are experimentally cumbersome and inefficient. Furthermore, known methods are typically limited to the production of a single labeled compound and no process has been described heretofore which would allow for the production of any desired labeled vitamin D compound by the same general experimental procedure. The process of the present invention provides such a general method. The process provides for the conversion of any unlabeled preformed vitamin D compound to the corresponding isotopically labeled (deuterium or tritium-labeled) form. The direct transformation of unlabeled to isotopically labeled vitamin D compounds and the complete generality of this conversion, are two unique features of this process. Furthermore the process yields vitamin D products labeled specifically at carbon 6 of the molecule with the heavy isotopes of hydrogen. Most of the known labeling processes yield side chain labeled vitamin D compounds where the label may be lost because of rapid side chain metabolism as discovered recently [Esvelt et al. Biochemistry 18, 3977 (1979); Wichmann et al. Biochemistry 18, 4775 (1979)]. Label location at carbon 6 is, therefore, highly advantageous and may be essential for certain applications. Another noteworthy aspect of this process is the production of both 6-labeled-vitamin D compounds (i.e. having the natural 5,6-cis double bond configuration) and 6-labeled-5,6-trans vitamin D compounds. Vitamin D metabolites labeled at carbon 6 can be used effectively in any of the metabolite assay procedures cited earlier.

The isotopically labeled products of this process are characterized by the structures below,

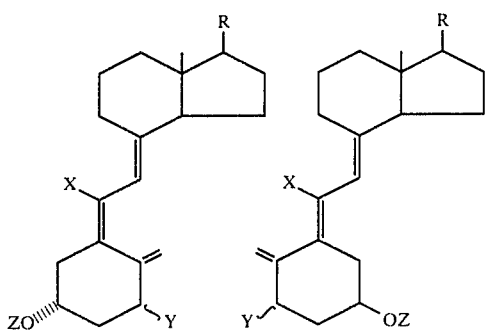

where the substituent X represents a heavy isotope of hydrogen, i.e. deuterium or tritium, and where Y represents hydrogen, hydroxy, or protected hydroxy, which may have either the $\alpha$ or $\beta$ stereochemical orientation, but is preferably $\alpha$, and where Z is hydrogen or acyl. In the above structures, R signifies any substituent which may be desired in the final product. Of primary interest are the steroid side chains, which can be substituted, unsubstituted, or saturated or unsaturated, although the present process is also fully applicable and functional which the much more simple side chains such as where R is hydrogen or alkyl. Examples of side chains which comport with the steroid configuration ar those where R represents the side chain of cholesterol or ergosterol or modified cholesterol or ergosterol side chains of the configuration:

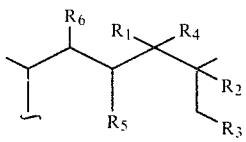

where each of $R_1$, $R_2$ and $R_3$ is selected from the group consisting of hydrogen, hydroxy, protected-hydroxy, alkyl and fluoro, and where $R_4$ represents hydrogen or alkyl, and where $R_5$ and $R_6$ are hydrogen or, when taken together, form a double bond, and where $R_1$ and $R_2$ or $R_2$ and $R_3$ when taken together form an epoxide, acetonide or cyclic-O-boronate grouping. A protected-hydroxy group is one in which the hydroxy group is present in derivatized form, for example, as an O-acyl, O-alkyl, O-alkylsilyl, O-benzyloxycarbonyl, O-tetrahydropyranyl, O-ethoxymethyl, or other O-($\alpha$-alkoxy)alkyl (e.g. O-($\alpha$-methoxy)ethyl) derivatives which are well-known in the art. In addition, the side chain R may represent hydrogen, or a saturated or unsaturated hydrocarbon radical which may be of straightchain or branched configuration, such as methyl, ethyl, propyl, isopropyl, butyl, isobutyl, pentyl, isopentyl, hexyl, vinyl, propenyl, butenyl, isobutenyl, pentenyl, dimethylallyl, hexenyl, etc., or R may represent other functionalized side chains, containing, for example, ester, acid or carbonyl functions, as represented by side chains of the configuration:

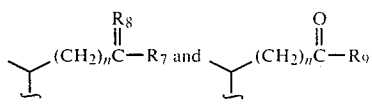

wherein $R_7$ is hydrogen or alkyl, $R_8$ is a carbonyl group or protected carbonyl group (e.g. dimethyl or diethylketal or acetal, or ethylene ketal or acetal), where $R_9$ is hydroxy or O-alkyl and n is an integer selected from 1, 2 and 3 (of which the side chains of cholenic acid or homocholenic acid and their alkyl esters, and of 24-keto-, or 25-ketonorcholesterols are specific embodiments).

In this specification and in the claims, the word "alkyl" denotes a saturated straightchain or branched hydrocarbon radical of 1-6 carbon atoms, such as methyl, ethyl, propyl, butyl, isopropyl, isobutyl, etc., or an unsaturated, straightchain or branched hydrocarbon (alkenyl) radical of 2-6 carbons, such as vinyl, propenyl, butenyl, isobutenyl, etc. and the word "acyl" denotes an aliphatic acyl group of 1-5 carbons such as formyl, acetal, propionyl or an aromatic acyl group such as benzoyl, nitrobenzoyl or halobenzoyl. In the preferred embodiment, R in the above structure has the configuration of the side chain of cholesterol, 25-hydroxycholesterol, 24,25-dihydroxycholesterol, 25,26-dihydroxycholesterol, or of ergosterol, or 25-hydroxyergosterol, X represents a tritium or deuterium atom, and Y represents hydrogen or a hydroxy group having the $\alpha$-configuration.

The novel labeling process of this invention comprises the introduction of tritium or deuterium label by reduction of a 6-keto-3,5-cyclovitamin D compound, itself derived from a preexisting vitamin D starting material as more fully described below. The 6-keto-3,5-cyclovitamin D compound used for label introduction is characterized by structure 1, below

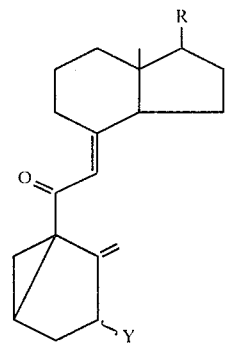

where R is a side chain as defined above, and where Y represents hydrogen, hydroxy or protected-hydroxy, (e.g. O-acyl or O-alkylsilyl).

Reduction is most effectively accomplished with deuterium- or tritium-labeled reagents specific for the reduction of a ketonic group to the corresponding alcohol. Reagents of choice are deutero- or tritio-borohydrides (e.g. $NaB^2H_4$ or $NaB^3H_4$) which are commercially available in highly deuterated or tritiated form (e.g. $\simeq 100\%$ deuterium, or up to 100 Ci/mmole tritium). With these reagents the reaction is conveniently conducted in an alcohol solvent (e.g. methanol, ethanol) at moderate temperatures (e.g. 25°–60° C.) using excess reducing reagent. Presumably because the ketone function is sterically somewhat hindered, quite long reaction times (several hours) are required for reduction with these reagents and conditions. The excess reagent is destroyed by addition of water and after extraction of this aqueous mixture with an organic solvent (e.g. ether, $CH_2Cl_2$, $CHCl_3$), the reduction product, the 6-hydroxy-6-X-cyclovitamin D compound (where X represents deuterium or tritium) is obtained in adequate purity for the subsequent reactions of the process. This product may be represented by the structure 2 below, where X is the isotopic label, and R and Y are substituents as defined for the starting material. Unlabeled products of this type, namely 6-hydroxy-3,5-cyclovitamin D compounds are known products (Scheves and Mazur, Tetrahedron Lett. 2987 (1976); DeLuca et al., U.S. Pat. No. 4,195,027).

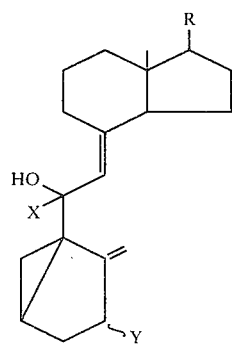

This labeled reduction product is then directly solvolyzed to yield, in admixture, 6-labeled 5,6-cis and 5,6-trans vitamin D products, characterized by the structures 3 and 4 below, where R, X and Y are substituents as defined above and where Z may be hydrogen or acyl, depending on solvolysis conditions chosen.

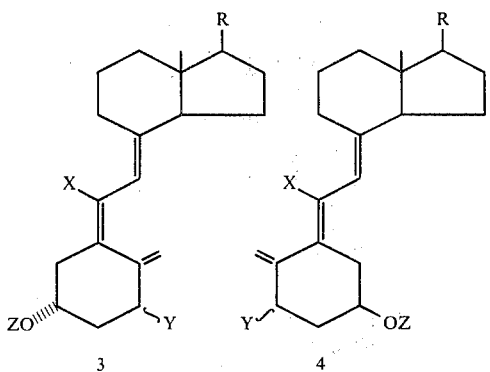

3    4

A preferred method of solvolysis consists of treating the 6-labeled-reduction product (structure 2 above) with warm (ca. 60°) glacial acetic acid for ca. 15-30 min. (i.e. the general conditions of DeLuca et al. in the co-pending application for U.S. Letters Patent Ser. No. 041,079) whereby a mixture (usually ca. 3:1) of the 6-labeled vitamin D 3-O-acetate derivative and the corresponding 5,6-trans isomer (structures 3 and 4, respectively, with Z=acetyl) are obtained. This solvolysis procedure is effective for all 6-hydroxy-cyclovitamin D compounds, and is recommended especially for the solvolysis of those compounds where Y is hydrogen or hydroxy. The alternative solvolysis methods described by Paaren et al. [Proc. Natl. Acad. Sci. USA 75, 2080 (1978)] and DeLuca et al. (U.S. Letters Patent 4,195,027) and of Sheves and Mazur (Tetrahedron Lett. 2987, 1976) e.g. solvolysis in formic acid or p-toluene sulfonic acid are, however, also useful. In those cases, for example, where Y in the 6-hydroxy cyclovitamin compound is an O-acyl group, solvolysis in aqueous p-toluenesulfonic acid, generating a mixture of 1-O-acyl-vitamin D and 1-O-acyl-5,6-transvitamin D products (i.e. the compounds of the general structures 3 and 4 where Y=O-acyl, and Z=H), is often advantageous, because the separation of cis and trans mixtures, in the case of 1,3-disubstituted compounds, is generally facilitated when one of the substituents (at either carbon 1 or 3) is a free hydroxy group.

The cis and trans products (compounds of structure 3 and 4) are separated chromatographically (e.g. by column chromatography, or thin layer chromatography, or high pressure liquid chromatography) or by crystallization to obtain the cis and trans isomers in pure form and (if acyl groups are to be removed) each is then subjected to mild basic hydrolysis using standard conditions (e.g. 5% KOH/methanol, 1-5 hr., 50°) to obtain the desired 6-deutero (tritio)-vitamin D product as well as the corresponding 6-deutero (tritio)-5,6-trans vitamin D isomer, both in pure form. Removal of acyl groups can, of course, also be accomplished efficiently, by the use of hydride reducing agents (e.g. lithium aluminum hydride) according to well-known procedures, provided there are no other reducible groups (e.g. ketone, ester, etc.) in the molecule, or unless simultaneous reduction of such reducible groups is desired. Removal of other hydroxy-protected groups (e.g. O-tetrahydropyranyl, O-alkylsilyl, etc.) as may be present in the side chain or at carbon 1, can, if desired, be accomplished in a separate step, by hydrolysis under mildly acidic conditions (e.g. hydrolysis in formic or acetic acid mixtures, or treatment with pyridinium p-toluenesulfonate in the presence of a hydroxylic solvent, at moderate temperatures (25°-50° C. for 1-24 hrs.) to obtain the corresponding deprotected vitamin D compounds.

Alternatively, removal of acyl or other protected groups, by base or acid hydrolysis or hydride reduction, can be accomplished prior to separation of the 5,6-cis and trans isomers resulting from solvolysis. For example, the solvolysis product mixture can be subjected directly to hydrolysis under basic conditions to produce the mixture of the corresponding free hydroxy compounds which are then separated by chromatography or crystallization to yield the desired labeled vitamin D products in pure form. In the case of 1,3-disubstituted compounds, separation of isomers prior to acyl group removal is in general the preferred procedure, however.

The isotopic labeling method described above produces specifically the 6-mono-deutero or 6-mono-tritio vitamin D compounds. In the case of deuterium labeling, the product is essentially 100% mono-deuterated, when commercial highly enriched deuteride reducing agents (e.g. commercial ca. 100% deuterated $NaB^2H_4$) are used. Similarly with highly enriched tritide reducing agents (e.g. $NaB^3H_4$ of specific activity of 75-100 Ci/mmole), products exhibiting a specific activity of greater than 10 Ci/mmole and, preferably greater than 20 Ci/mmole are readily prepared. Generally preferred products of this process are 6-labeled-vitamin D compounds (i.e. having the natural 5,6-cis geometry) where substituent Y, if present, is in the natural α-configuration. However, 6-labeled-5,6-trans compounds are also of interest and utility, for example in studies of metabolism and tissue distribution of 5,6-trans vitamin D compounds, some of which, e.g. trans vitamin $D_3$ and 25-hydroxy-5,6-trans vitamin $D_3$ are known to be biologically active. Furthermore, 6-labeled-5,6-trans compounds are, of course, convertible to the 5,6-cis isomers by photochemical isomerization (with or without photosensitizer) of the 5,6-double bond. Similarly 6-labeled vitamin D compounds (5,6-cis or 5,6-trans) where the C-1-substituent Y (if present) is in the unnatural β-configuration are of considerable scientific interest for comparative studies in metabolism, enzymology and tissue distribution and excretion which, in contributing to knowledge concerning the importance of stereochemical configuration at carbon 1, can be expected to have important practical benefits for the design and production of analogs with specific biological properties. Labeled 1β-substituted products are readily produced by subjecting 1β-substituted 6-keto-cyclovitamin D compounds to the labeling process described above.

The 6-keto-cyclovitamin D materials required for label introduction (general structure 1, above) can be prepared from the corresponding vitamin D compounds, although as described below, the exact process chosen depends on the starting material available and the nature and/or configuration of the substituent Y at carbon 1 desired. 6-Keto-cyclovitamin D compounds bearing no substituent at carbon 1 (i.e. compounds of structure 1 above where Y is hydrogen) are conveniently prepared from vitamin D compounds, having the general structure 5 below:

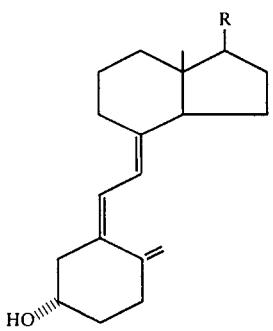

Such vitamin D compounds are readily available as synthetic or natural products, e.g. vitamin $D_3$, vitamin $D_2$, 25-hydroxyvitamin $D_3$, 25-hydroxyvitamin $D_2$, 24,25-dihydroxyvitamin $D_3$, 25,26-dihydroxyvitamin $D_3$, etc., as well as other vitamin D side chain analogs and derivatives, as listed for example by DeLuca et al. in "Topics in Current Chemistry", Vol. 83, Biochemistry, p. 1–66, Springer Verlag, New York, 1979.

For the preparation of 6-keto-cyclovitamin D products, the vitamin D compounds above are first converted to the known 6-hydroxy-3,5-cyclovitamin D compounds by a two-step process involving tosylation of C-3-hydroxy group followed by aqueous bicarbonate-buffered solvolysis of the 3-O-tosyl intermediate, as described by Paaren et al. (ref. cited), or DeLuca et al. (patents cited), or Sheves and Mazur, Tetrahedron Letters 2987 (1976). The resulting product is characterized by the general structure 6 below

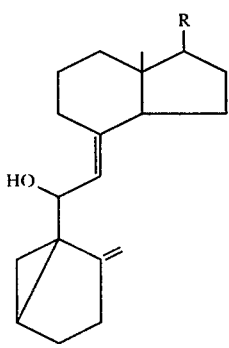

This 6-hydroxy-cyclovitamin D intermediate is then oxidized at carbon 6 to yield the desired 6-keto-3,5-cyclovitamin D product illustrated by the formula 7 below (which corresponds to formula 1 illustrated previously, where Y=hydrogen),

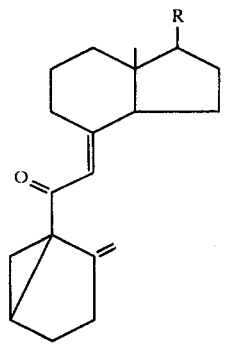

where R is a steroid side chain as defined earlier. Activated manganese dioxide (as used by Sheves and Mazur for the preparation of 6-ketocyclovitamin $D_3$ in Tetrahedron Letters 2987 (1976)) is an effective oxidant for accomplishing the transformation but the conditions and experimental procedures depend critically on the nature and substitution pattern of other functionalities present in the molecule. It has been found that certain structural units are not compatible with the use of this particular oxidant, e.g., allylic primary or secondary hydroxy groups are oxidized. It has also been unexpectedly found that vicinal diols in the steroid side chain (e.g. 24,25-dihydroxy-, and 25,26-dihydroxy structures) undergo oxidative cleavage with manganese dioxide under conditions required for the oxidation of the 6-hydroxy group. Isolated hydroxy functions are not affected. Oxidative cleavage of diols can be prevented by protection (e.g. acylation, alkylsilylation, etc.) of at least one of the hydroxy groups involved. Such protection is best accomplished by alkylsilylation or acetylation either prior to, or immediately after, the formation of the 3-O-tosyl derivative as described above. These O-protecting groups are generally retained throughout the process to be removed after formation of the 6-labeled vitamin derivatives in a final hydrolysis or reduction step (depending on the protecting group chosen), but may, if desired, be also removed immediately after formation of the 6-keto-cyclovitamin intermediate. For example, for the preparation of 6-labeled 24,25-dihydroxyvitamin $D_3$ the following sequences may be employed. The starting material 24,25-dihydroxyvitamin $D_3$ is first silylated by treatment with tert-butyldimethylsilylchloride in dimethylformamide/imidazole for 24 hr at 40°–50° C. to produce 24,25-dihydroxyvitamin $D_3$ 3,24-di(tert-butyldimethylsilyl) ether. The alkylsilyl group at the 3-position is subsequently removed by mild hydrolysis in acetic acid/tetrahydrofuran/$H_2O$ (3:1:1) at ca. 30° C. for six hours to give the desired 24-monoalkylsilylated product which is then tosylated under the usual conditions to the 3-O-tosyl intermediate. Subsequent solvolysis as previously described yields the 6-hydroxy-3,5-cyclovitamin D compound which may now be safely oxidized with manganese dioxide to yield 6-oxo-24,25-dihydroxy-3,5-cyclovitamin $D_3$ 24-tert-butyldimethylsilyl ether. The same product can also be obtained by initial tosylation of 24,25-dihydroxyvitamin $D_3$ to the 3-O-tosyl derivative, followed by alkylsilylation under the conditions described above to give to 3-O-tosyl-24-O-tert-butyldimethylsilyl derivative which is then solvolyzed and oxidized to the 24-protected-6-keto product.

If desired, the protecting group of C-24 may now be removed, for example, by hydrolysis under mild acidic conditions (acetic acid/THF/H$_2$O, 3:1:1, at 55° C. for 24 hr), the resulting 24,25-dihydroxy-6-oxo-cyclovitamin product then being carried through the labeling process as previously described. Alternatively, the C-24-hydroxy protecting group may be left intact until label introduction (by reduction of the 6-ketone) and subsequent solvolytic cycloreversion has been accomplished, the protecting group being finally removed (using the hydrolysis conditions given above) either directly after solvolysis, or after the separation of the 5,6-cis and trans products (resulting from solvolysis). If the solvolysis conditions chosen result in the formation of 3-O-acyl derivatives (see above), these acyl groups are, as described earlier, removed in a separate (hydrolytic or reductive) step either prior, or subsequent to, the removal of the C-24-protecting group. For the protection of sensitive hydroxy functions, acyl protecting groups or tetrahydropyranyl protecting groups are of course also useful. For example, 24,25-dihydroxyvitamin D$_3$ 3-O-tosylate can be acetylated at C-24 by treatment with acetic anhydride in pyridine overnight, and the resulting product (the 24-acetoxy derivative) is then solvolyzed and oxidized to the desired 6-keto-24,25-dihydroxy-3,5-cyclovitamin D$_3$ 24-acetate. After label introduction and solvolytic cycloreversion, the acyl protecting groups are readily removed (preferably by hydride reduction). For the special case of vicinal diols, effective protection can, of course, also be accomplished by the formation of cyclic boronate or cyclic isopropylidene (acetonide) derivatives. For example, treatment of a vicinal diol (e.g. 24,25-dihydroxyvitamin D$_3$) with phenylboronic acid in tetrahydrofuran at room temperature yields the corresponding cyclic O-boronate ester (e.g. 24,25-O-phenylboronate ester).

The manganese dioxide oxidation of 6-hydroxy-cyclovitamin D compounds to the required 6-keto-derivatives is accomplished with excess activated manganese dioxide in a halo-carbon solvent (e.g. CH$_2$Cl$_2$, CHCl$_3$) at room temperature over a period of 10-20 hours or, preferably, in benzene at elevated temperatures (ca. 60°) for 4-6 hours. The 6-keto-cyclovitamin D product, having the structure shown above (formula 7), can be isolated by column, thin-layer or high pressure liquid chromatography, or crystallization in adequate purity for use in the isotope labeling process described earlier.

For the preparation of 1-hydroxy-6-keto-cyclovitamin D compounds or 1-(protected-hydroxy)-6-keto-cyclovitamin D compounds of structure 1 above, where Y is hydroxy or protected-hydroxy (preferably O-acyl or O-alkylsilyl) a convenient novel method, involving the allylic oxidation of a 1-deoxy-6-keto-cyclovitamin D compound (i.e. compounds of general structure 7 shown above) with selenium dioxide and t-butyl hydroperoxide, has been developed. Under these allylic oxidation conditions 1-hydroxylated product can be prepared from the corresponding 1-deoxy-6-ketocyclovitamin precursor. This product is characterized by structure 8 below, where Z is hydrogen. Simple acylation of the hydroxy compound by standard methods, yield, if desired, the corresponding 1-O-acyl derivatives characterized by structure 8, where Z=acyl, and other 1-O-protected derivatives (e.g. 1-O-alkylsilyl, 1-O-tetrahydropyranyl, etc.) are, of course, also readily prepared by procedures shown in the art.

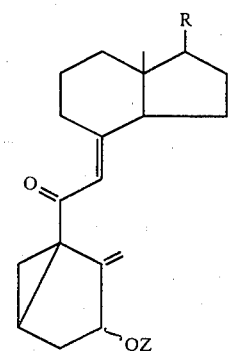

8

A noteworthy feature of this oxidation process is its selectivity in that C-1-oxygenated product is formed essentially exclusively in spite of the presence of an $\alpha,\beta$-unsaturated ketone function with two activated allylic positions (at C-10 and C-14) susceptible to oxidation. In this respect the outcome of the reaction is similar to that of the allylic oxidation process described by DeLuca et al. in U.S. Pat. No. 4,195,027 although that disclosure does not apply to compounds containing an unsaturated 6-ketone unit. The stereochemical outcome of the present process is, however, quite different from that of DeLuca et al. Whereas DeLuca et al. obtain 1$\alpha$-hydroxy-product essentially exclusively, the process of the invention gives predominantly the 1$\beta$-hydroxy-6-keto-cyclovitamin D compounds. Thus the allylic oxidation product (compound 8, where Z=hydrogen) consists of a ca. 1:2 mixture of 1$\alpha$-hydroxy- and 1$\beta$-hydroxy-6-keto-cyclovitamin D compounds. If desired, the 1$\alpha$ and 1$\beta$-epimers may be separated. A convenient separation procedure consists of converting the hydroxyepimers to the corresponding 1-O-protected derivatives (e.g. the 1-acetates, as represented by structures 8 with Z=acetyl, readily prepared by treating the hydroxy compound mixture with acetic anhydride in pyridine at room temperature) which are easily separated into the 1$\alpha$-O-acyl- and 1$\beta$-O-acyl constituents by standard high pressure liquid chromatography on silica gel columns. Each epimer may then be subjected to the labeling process described above. For the purposes of the isotopic labeling process it is not necessary, however, to separate the epimers at this stage. It is indeed often preferred to subject the mixture of 1$\alpha$ and 1$\beta$-epimers to the first step of the isotopic labeling process (i.e. label introduction by borotritide (-deuteride) reduction), thereby obtaining the 6-hydroxy-6-labeled-cyclovitamin D intermediate (as a mixture of the 1$\alpha$ and 1$\beta$-hydroxy epimers), and to subject this mixture in turn to solvolysis in glacial acetic acid to obtain a total of four 6-labeled products; namely, the 1$\alpha$-hydroxy-3-O-acyl vitamin D and the 1$\beta$-hydroxy-3-O-acyl vitamin D compounds and the corresponding 5,6-trans-1$\alpha$- and 1$\beta$-epimers. Chromatographic separation of this mixture (preferably by high pressure liquid chromatography) and subsequent acyl removal provides 6-labeled 1$\alpha$-hydroxyvitamin D product and the corresponding 5,6-trans-isomer, as well as, if desired, 6-labeled 1$\beta$-hydroxyvitamin D and its 5,6-trans-isomer.

It is evident from the foregoing and from the specific examples which follow that the process of this invention provides a general method for the conversion of any vitamin D compound (bearing a hydroxy at carbon 3) to the corresponding labeled derivative bearing tritium or deuterium at the 6-position. In particular, the process can be used advantageously for converting any of the known vitamin D metabolites to their 6-labeled forms. Thus, 6-tritio (deutero)-vitamin $D_3$, 25-hydroxyvitamin $D_3$, 1,25-dihydroxyvitamin $D_3$, 24,25-dihydroxyvitamin $D_3$, 25,26-dihydroxyvitamin $D_3$ or 1,24,25-dihydroxyvitamin $D_3$ are readily prepared from the unlabeled metabolites, and 6-tritio (deutero)-derivatives of the vitamin $D_2$ series are also easily accessible. Similarly the novel side chain-modified metabolites discovered recently, e.g. calcitroic acid or 25-hydroxyvitamin $D_3$-26,23-lactone (Esvelt et al.; Wichmann et al., refs. cited) can be converted to their 6-labeled derivatives by this process. It is also evident that the combination of the 6-labeling process with allylic C-1-hydroxylation provides a versatile route to both 1-deoxy- and 1-hydroxylated-6-labeled vitamin D (having the 1α or 1β stereochemistry) products from a single unlabeled precursor. For example, 6-labeled-1α,25-dihydroxyvitamin $D_3$ and 6-labeled-1α,25-dihydroxy-5,6-trans-vitamin $D_3$ as well as 6-labeled-1β,25-dihydroxyvitamin $D_3$ and its 5,6-trans isomer can be produced from unlabeled 25-hydroxyvitamin $D_3$, which in addition also serves as starting material for 6-labeled-25-hydroxyvitamin $D_3$ and its 5,6-transisomer.

This flexibility in terms of starting material chosen and labeled product to be produced is a unique feature of this present process. This versatility can be exploited also for the preparation of doubly-labeled vitamin D compounds. For example, vitamin D analogs of general structure 9 below, where Y is hydrogen or hydroxy and R is any of the sidechain A, B, C, D, or E shown

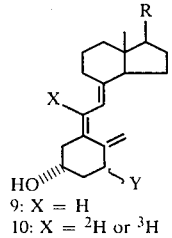
9: X = H
10: X = $^2$H or $^3$H

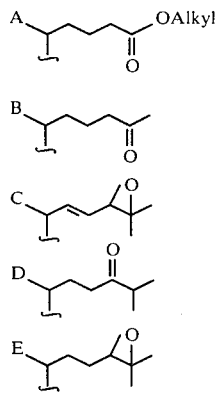

can be labeled by means of the present process with deuterium or tritium (a sidechain of type B or D being suitably protected, e.g. via the ethylene ketal, to avoid ketone reduction) to give 6-labeled derivatives of general structure 10, which in turn are reacted with $^{13}$C- or $^{14}$C- or $^2$H- or $^3$H-labeled methyl-Grignard reagents (as described by DeLuca et al. in co-pending application for U.S. Letters Patent, Ser. No. 041,080 and by Napoli et al. Anal. Biochem. 96, 481 (1979)) to give 25-hydroxylated products labeled at both C-6 and in the sidechain, as illustrated by the side chain structures below, arising from sidechains of type A, B, C, D and E respectively, where L represents a labeled alkyl group, e.g. $^{14}CH_3$, $^{13}CH_3$, $C^2H_3$, $C^3H_3$.

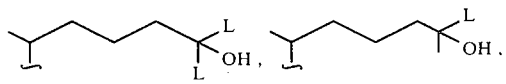

-continued

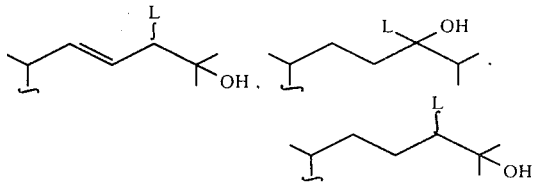

Alternatively, the side chains of type A, B, C, D or E can of course also be reduced with isotopically labeled hydride reducing reagents to give the corresponding C-24 or C-25-labeled (deuterated, tritiated) hydroxylated side chain analogs. Vitamin D compounds of structure 9, possessing side chains of type A or B are described in the co-pending application of DeLuca et al., Ser. Nos. 041,080 and 041,081; similarly 24-ketovitamin $D_3$ (side chain of type D) is described by Tanaka et al., Arch. Biochem. Biophys. 177, 615 (1976); the vitamin analog with the side chain of type C can be prepared by known methods from the steroid possessing that side chain (Salmond et al., J. Org. Chem. 43, 790 (1978)), and the vitamin compound featuring the sidechain of type E can be prepared from desmosteral, via i-ether formation, 24,25-epoxidation and subsequent conversion of steroid to the vitamin triene by standard methods. Combination of the 6-labeling process with allylic oxidation at C-1 as described in the foregoing then provides also any of the C-1 hydroxylated double-labeled vitamin D compounds.

The following specific examples, in which all temperatures are expressed in °C., are intended to be illustrative only and are not to be construed as limiting the scope of the appended claims.

EXAMPLE 1

Preparation of [6-$^2$H]-vitamin $D_3$ and 5,6-trans-[6-$^2$H]-vitamin $D_3$.

(a) 6-hydroxy-3,5-cyclovitamin $D_3$

To 100 g of vitamin $D_3$ in 2.0 ml of dry pyridine is added 100 mg of p-toluenesulfonyl chloride. The reaction is stirred at room temperature for 6–8 hr, poured over ice/$H_2O$ and extracted with ether. The ether extracts are washed with 1 N HCl, sat. $NaHCO_3$, sat. NaCl and dried over $MgSO_4$. Removal of the solvent in vacuo yields the crude tosylate which is satisfactory in the following reaction. The $D_3$-tosylate is suspended in 20 ml of acetone:$H_2O$ (9:1) along with 300 mg of $NaHCO_3$ and heated to 60° for 24 hr. The cooled reaction is concentrated in vacuo and extracted with ether. The organic extracts were washed with $H_2O$, dried over $MgSO_4$ and concentrated to a crude oil which is chromatographed on a 750μ silica gel tlc plate in 1:4 ethyl acetate:hexane to yield 50 mg of 6-hydroxy-3,5-cyclovitamin $D_3$: mass spectrum, (m/e): 384 (M$^+$, 28), 366 (55), 271 (25), 253 (45), 247 (75), 135 (100).

(b) 6-oxo-3,5-cyclovitamin $D_3$

To 30 mg of 6-hydroxy-3,5-cyclovitamin $D_3$ in 10 ml of dry, distilled benzene is added 300 mg of activated $MnO_2$ in small portion over a 4 hr period while the reaction is maintained at 60°. The reaction is continued for 2.0 hr, cooled and filtered through celite. The solvent is removed in vacuo and the residue is purified by tlc (750μ silica gel plate, (9:1) hexane: ethyl acetate) to yield 23 mg of 6-oxo-3,5-cyclovitamin D: UV: $\lambda_{max}$ 252 nm, ε=13,000; mass spectrum, (m/e): 382 (100), 367 (25) 269 (35), 247 (40), 135 (95), 133 (75); nmr (δ): 0.57 (3H, s, 18—CH$_3$), 0.88 and 0.86 (6H, d, J=5.8 Hz, 26—CH$_3$ and 27—CH$_3$), 6.93 and 0.91 (3H, d, J=6.2 Hz, 21—CH$_3$), 5.01 (1H, s, 19(Z)—H), 5.20 (1H, s, 19(E)-H), and 6.06 (1H, s, 7—H).

(c) [6-$^2$H]-6-hydroxy-3,5-cyclovitamin D$_3$

To a solution of 3.0 mg of 6-oxo-3,5-cyclovitamin D$_3$ in 300 μl of ethanol is addd 300 μl of a saturated solution of NaB$^2$H$_4$ in ethanol. The reaction is heated to 55°-65° for 12 hr, cooled, quenched with H$_2$O and extracted with ether. The ether extracts are washed once with water, dried over MgSO$_4$ and concentrated in vacuo to yield 2.8 mg of [6-$^2$H]-6R and 6S-hydroxy-3,5-cyclovitamin D$_3$: mass spectrum (m/e): 385 (M$^+$, 25), 367 (60), 272 (20), 254 (40) 247 (70) 135 (70), 119 (100).

(d) [6-$^2$H]-vitamin D$_3$ and 5,6-trans-[6-$^2$H]-vitamin D$_3$

A solution of 2.0 mg of [6-$^2$H]-6-hydroxy-3,5-cyclovitamin D$_3$ in 250 μl of glacial acetic acid is heated to 55° for 15 min, cooled and quenched with ice/NaHCO$_3$. After extracting with ether, the organic solution is washed with water, dried over MgSO$_4$ and treated with a small amount of LAlH$_4$. The reduction is terminated after 10 min at room temp. by the addition of a few drops of 5% NaOH/H$_2$O, and the solution is dried with MgSO$_4$ and concentrated in vacuo. The resulting crude oil is chromatographed on a 5 cm×20 cm 250μ silica gel plate, (1:4) ethyl acetate-hexane to yield 600 μg of [6-$^2$H]-5,6-trans-vitamin D$_3$ [UV: λ$_{max}$=272 nm, ε=24,000; mass spectrum, (m/e): 385 (M$^+$, 30), 137 (80), 119 (100)] and 1.0 mg of [6-$^2$H]-vitamin D$_3$: UV: λ$_{max}$=264, nm, ε=18,000; mass spectrum, (m/e): 385 (M$^+$, 15), 352 (5), 137 (95), 119 (100); nmr (δ): 0.54 (3H, s, 18-CH$_3$), 0.86 and 0.88 (6H, d, J=6.2 Hz, 26—CH$_3$ and 28—CH$_3$), 0.91 and 0.93 (3H, d, J=6.6 Hz, 21—CH$_3$), 3.96 (1H, m, 3α-H), 4.82 (1H, m(sharp), 19(Z)-H), 5.05 (1H, m(sharp), 19(E)—H) and 6.03 (1H, s, 7—H).

Utilizing sodium borotritide as the reductant (step c) in a procedure similar to the above, there is obtained [6-$^2$H]-vitamin D$_3$ and 5,6-trans-[6-$^3$H]vitamin D$_3$.

EXAMPLE 2

Preparation of [6-$^3$H]-vitamin D$_2$ and 5,6-trans-[6-$^3$H]-vitamin D$_2$.

(a) 6-hydroxy-3,5-cyclovitamin D$_2$

To 10 mg of vitamin D$_2$ in 200μ l of dry pyridine was added 10 mg of p-toluenesulfonyl chloride. After 18 hr the reaction was poured over ice/H$_2$O, extracted with ether; the ether extracts were washed with 1 N HCl, sat. NaHCO$_3$, water, dried over MgSO$_4$ and concentrated in vacuo.

The crude vitamin D$_2$-tosylate was suspended in 6 ml of acetone:water (9:1) containing 30 mg of NaHCO$_3$ and heated to 60° for 18 hr. After this time the reaction is cooled, concentrated in vacuo and extracted with ether. The organic extracts are washed with water, dried over MgSO, and taken to an oil in vacuo. Preparative tlc, 750μ plate 3:1 hexane:ethyl acetate, affords 6.5 mg of (6R)-6-hydroxy-3,5-cyclovitamin D$_2$: mass spectrum m/e: 396 (M$^+$, 20), 281 (15), 378 (15), 271 (20), 253 (35), 135 (50), 119 (60) 69 (100); nmr (δ): 0.55 (3H, s, 18—CH$_3$), 0.67 (1H, m, C—4), 0.82 (6H, m, 26—CH$_3$ and 27—CH$_3$), 0.91 and 0.93 (3H, d, J=6.4 Hz, 21—CH$_3$), 1.00 and 1.03 (3H, d, J=6.6 Hz, 28—CH$_3$), 4.94 (3H, m(sharp), 6—H, 19(E) and 19(Z)—H), 4.98 (1H, s, 7—H) and 5.19 (2H, m, 22—H and 23—H).

(b) 6-oxo-3,5-cyclovitamin D$_2$

To 6.5 mg of 6-hydroxy-3,5-cyclovitamin D$_2$ in 1.0 ml of benzene is added 65 mg of activated MnO$_2$ in small portions over a 4 hr period while the reaction is maintained at 60°. After 2.0 hr longer at this temp., the reaction is filtered through celite and concentrated in vacuo. The crude product is purified by tlc to yield 4.2 mg of 6-oxo-3,5-cyclovitamin D$_2$: UV: λ$_{max}$=252 nm, ε=13,000; mass spectrum, m/e: 394 (M$^+$, 100), 269 (40), 135 (70), 133 (60), 69 (70); nmr (δ): 0.58 (3H, s, 18—CH$_3$), 0.84 (6H, m, 26—CH$_3$ and 27—CH$_3$), 0.90 and 0.93 (3H, d, J=6.6 Hz, 21—CH$_3$), 1.01 and 1.03 (3H, d, J=6.6 Hz, 28—CH$_3$), 5.01 (1H, s, 19(Z)—H), 5.20 (3H, m, 19(E)—H, 22—H and 23—H), 6.05 (1H, s, 7—H).

(c) [6-$^3$H]-vitamin D$_2$ and 5,6-trans-[6-$^3$H]-vitamin D$_2$

To 500 μg of 6-oxo-3,5-cyclovitamin D$_2$ in 300 μl of 100% EtOH is added a three molar excess of NaB$^3$H$_4$ (48 Ci/mmole) in 200 μl of EtOH and the reaction is heated at 60° for 12.0 hr. The cooled mixture is quenched with 1.5 ml of H$_2$O at room temp. for 20 min then extracted with ether. The organic phase is dried over MgSO$_4$, filtered into a small conical tube and evaporated to dryness under a stream of N$_2$. This product is then treated with 200 μl of glacial acetic acid for 15 min at 55°, cooled, quenched with ice/sat. NaHCO$_3$ and extracted with ether. The dried ether extracts are treated with a few drops of LAlH$_4$/Et$_2$O to remove the 3β-acetoxy function and after workup chromatographed on a 5×20 cm 250μ silica gel plate to yield 5,6-trans-[6-$^3$H]-vitamin D$_2$ (12 ci/mmole) which co-chromatographs with an authentic cold standard on hplc (1.5% 2-propanol/hexane 6.2 mm×25.0, Zorbax-SIL) at 20.5 ml elution volume, and [6-$^3$H]-vitamin D$_2$ (12 Ci/mmole) which also co-chromatographs with an authentic sample at 37 ml elution volume on the hplc system described above.

EXAMPLE 3

Preparation of [6-$^2$H]-25-hydroxyvitamin D$_3$ and [6-$^2$H]-25-hydroxy-5,6-trans-vitamin D$_3$ (a) 6,25-dihydroxy-3,5-cyclovitamin D$_3$ By selective 3β-tosylation and aqueous buffered solvolysis using the conditions described in Examples 1a or 2a, 6,25-dihydroxycyclovitamin D$_3$ is produced in overall 55% yield from 25-hydroxyvitamin D$_3$ and possesses the following analytical parameters: mass spectrum, m/e: 400 (M$^{30}$, 5), 382 (35), 367 (10), 364 (15), 253 (30), 245 (25), 135 (60), 119 (65), 59 (60): nmr (δ): 0.55 (3H, s, 18—CH$_3$), 0.67 (1H, m, C—4) 0.94 and 0.95 (3H, d, J=5.9 Hz, 21—CH$_3$), 1.21 (6H, s, 26—CH$_3$) and 27—CH$_3$), 4.94 (3H, m(sharp), 6—H, 19(E)—H and 19(Z)—H), 4.98 (1H, s, 7—H).

(b) 6-oxo-25-hydroxy-3,5-cyclovitamin D$_3$

Oxidation of 6,25-(OH)$_2$-3,5-cyclovitamin D$_3$ with MnO$_2$ as described in Example 1b gives a 70% yield of 6-oxo-25-hydroxy-3,5-cyclovitamin D$_3$: UV: λ$_{max}$=252 nm, ε=13,000; mass spectrum m/e: 398 (M$^+$, 100), 383 (20), 380 (20), 269 (30), 245 (35), 135 (85), 133 (80), 59 (70); nmr (δ): 0.57 (3H, s, 18—CH$_3$), 0.93 and 0.95 (3H, d, J=5.9 Hz, 21—CH$_3$), 1.01 (1H, m, C—4), 1.2 (6H, s, 26—CH$_3$ and 27—CH$_3$), 5.01 (1H, m (sharp), 19 (Z)—H), 5.20 (1H, m, 19(E)—H) and 6.05 (1H, s, 7—H).

(c) 25-hydroxy-[6-$^2$H]-vitamin D$_3$ and 25-hydroxy-W5,6-trans-[6-$^2$H]-vitamin D$_3$.

Reduction of the 6-oxo-25-hydroxy-3,5-cyclovitamin with NaB$^2$H$_4$ (using the conditions described in Example 1c) followed by cycloreversion in glacial acetic acid and brief treatment with LiAl $^2$H$_4$ (as described in Example 1d) yields after separation by high-pressure liquid chromatography (silica-gel column, 5% 2-propanol/hexane) 25-hydroxy-[6-$^2$H]-vitamin D$_3$: UV: $\lambda_{max}$=265 nm, $\epsilon$=18,000; mass spectrum, m/e: 401 (M$^+$, 15), 383 (3), 368 (5), 137 (90), 119 (100), 59 (60); nmr ($\delta$): 0.54 (3H, s, 18—CH$_3$), 0.93 and 0.95 (3H, d, J=5.9 Hz, 21—CH$_3$), 1.21 (6H, s, 26—CH$_3$ and 27—CH$_3$), 3.95 (1H, m, 3$\alpha$—H), 4.82 (1H, m (sharp), 19(Z)—H), 5.05 (1H, m(sharp), 19(E)—H) and 6.03 (1H, m, 7—H), and 25-Hydroxy-5,6-trans-[6-$^2$H]-vitamin D$_3$: UV: $\lambda_{max}$=274 nm, $\epsilon$=24,000; mass spectrum, m/e: 401 (M$^+$, 25), 383 (10), 137 (85), 119 (100), 59 (65).

With sodium borotritide as reductant in the above procedure, 25-hydroxy-[6-$^3$H]-vitamin D$_3$ and its 5,6-trans-isomer are similarly obtained. In a similar fashion, from 25-hydroxyvitamin D$_2$ there is obtained 6-oxo-25-hydroxy-3,5-cyclovitamin D$_2$ according to steps a and b above, and this intermediate when reduced with sodium borotritide according to the procedure of step c above yields 25-hydroxy-[6-$^3$H]-vitamin D$_2$ and 25-hydroxy-5,6-trans-[6-$^3$H]-vitamin D$_2$. Likewise, from 26,27-dinorvitamin D$_3$-25-carboxylic acid methyl ester, there is obtained the corresponding 6-oxo-3,5-cyclovitamin D$_3$ derivative according to steps a and b above, which after borotritide reduction and solvolysis according to the general procedure of step c above provides 26,27-dinor[6-$^3$H]-vitamin D$_3$-25-carboxylic acid ester and its 5,6-trans-isomer.

EXAMPLE 4

Preparation of [6-$^2$H]-1$\alpha$-hydroxyvitamin D$_3$, [6-$^2$H]-1$\beta$-hydroxyvitamin D$_3$ and their 5,6-trans-isomers.

(a) 1$\alpha$ and 1$\beta$-hydroxy-6-oxo-3,5-cyclovitamin D$_3$

To 2.2 mg of SeO$_2$ in 3 ml of CH$_2$Cl$_2$ is added 20 $\mu$l of t-BuOOH ($\simeq$90%) and the reaction is stirred for 15 min at room temp. then cooled to 5° and 15 mg of 6-oxo-3,5-cyclovitamin D$_3$ (see Example 1b) is added in 1.0 ml of CH$_2$Cl$_2$. The reaction is allowed to warm to $\simeq$20° over 1.0 hr then quenched with 10% NaOH. This mixture is diluted with ether and washed with 10% NaOH, H$_2$O, dried over MgSO$_4$ and concentrated to a crude oil which is purified via tlc in 30% ethyl acetate:hexane to yield 8 mg of a 2:1 mixture of 1$\beta$ and 1$\alpha$-hydroxy-6-oxo-3,5-cyclovitamin D$_3$: UV: $\lambda_{max}$ 252, $\epsilon$=12,500; mass spectrum, m/e: 398 (M$^+$, 90), 285 (15), 267 (10), 151 (75), 135 (70), 133 (60); nmr ($\delta$): 0.57 (3H, s, (1$\beta$) 18—CH$_3$), 0.56 (3H, s, (1$\alpha$) 18—CH$_3$), 4.29 (1H, m, 1$\beta$—H), 4.66 (1H, m, 1$\alpha$—H).

Treatment of this product with acetic anhydride in pyridine (5 hr, room temp.) provides the corresponding 1-acetate derivatives (m/e/440, m$^+$). Treatment of the 1-hydroxy-6-oxocyclovitamin D$_3$ product with t-butyldimethylsilyl chloride in dimethylformamide containing imidazole (overnight, room temp.) yields the corresponding 1-O-t-butyldimethylsilyl ethers.

(b) 1$\alpha$- and 1$\beta$-hydroxy-[6-$^2$H]vitamin D$_3$-3-acetate and 1$\alpha$- and 1$\beta$-hydroxy-5,6-trans-[6-$^2$H]-vitamin D$_3$ 3-acetate To 3.0 mg of 1-hydroxy-6-oxo-3,5-cyclovitamin D$_3$ as obtained above, in 0.5 ml of ethanol is added 500 $\mu$l of a saturated solution of NaB$^2$H$_4$ in ethanol. The reaction is warmed to 60° for 16 hr, cooled, quenched with water at room temp for 15 min and extracted with ether. The dried ether extracts are taken to dryness and treated with 500 $\mu$l of glacial acetic acid at 55° for 15 min, cooled, quenched with ice/sat. NaHCO$_3$ and extracted with ether. The organic extracts are washed with water, dried over MgSO$_4$, concentrated in vacuo and chromatographed via hplc (1.5% 2-propanol/hexanes, 6.2 nm $\times$ 25 cm Zorbax-SIL) to yield 1.2 mg of [6-$^2$H]-1$\beta$-hydroxyvitamin D$_3$ 3-acetate: UV: $\lambda_{max}$=264 nm, $\epsilon$=18,000; mass spectrum, m/e: 554 (M$^+$, 10), 383 (80), 135 (100); nmr ($\delta$); 0.53 (3H, s, 18—CH$_3$), 0.86 and 0.88 (6H, d, J=6.6 Hz, 26—CH$_3$ and 27—CH$_3$), 0.91 and 0.93 (3H, d, J=5.9 Hz, 21—CH$_3$), 2.06 (3H, s, 3$\beta$—OCO CH$_3$), 4.18 (1H, m, 1$\alpha$—H), 4.98 (1H, m, 3$\alpha$—H), 5.00 (1H, m (sharp), 19(Z)—H), 5.34 (1H, m (sharp), 19(E)—H), 6.00 (1H, s, 7—H) which is eluted at 48 mls, followed by 0.5 mg of [6-$^2$H]-1$\alpha$-hydroxyvitamin D$_3$ 3-acetate: UV: $\lambda_{max}$=264 nm, $\epsilon$=18,000; mass spectrum, m/e 443 (M$^+$, 12), 383 (85), 135 (100). NMR ($\delta$): 0.54 (3H, s, 18—CH$_3$), 0.86 and 0.88 (6H, d, J=6.6 Hz, 26—CH$_3$ and 27—CH$_3$), 0.91 and 0.93 (3H, d, J=5.9 Hz, 21—CH$_3$), 2.03 (3H, s, 3—OCO CH$_3$), 4.41 (1H, m, 1$\beta$—H), 5.02 (1H, m (sharp), 19(Z)—H), 5.21 (1H, m, 3$\alpha$—HO, (1H, m, 3$\alpha$—H), 5.34 (1H, m (sharp), 19(E)—H), 6.02 (1H,s,7—H) eluting at 52 mls. [6-$^2$H]-1$\beta$-hydroxy-5,6trans-vitamin D$_3$ acetate: UV: $\lambda_{max}$ 269 nm elutes at 56 mls, followed by [6-$^2$H]-1$\alpha$-hydroxy-5,6-trans-vitamin D$_3$ acetate: UV: $\lambda_{max}$=270 nm, eluting at 60 mls.

(c) [6-$^2$H]-1$\alpha$- and 1$\beta$-hydroxyvitamin D$_3$ and 1$\alpha$- and 1$\beta$-hydroxy5,6-trans-vitamin D$_3$ Treatment of each of the four 3$\beta$-acetoxy vitamin isomers obtained from the preceeding reaction with LiAlH$_4$ removes the acetyl group and consistently provides the corresponding 1,3-diols in >90% yields. [6-$^2$H]-1$\alpha$-hydroxyvitamin D$_3$: UV $\lambda_{max}$=264 nm, $\epsilon$=18,000, mass spectrum, m/e: 401 (M$^+$, 15), 383 (15), 365 (10), 153 (30), 135 (100). [6-$^2$H]-1$\beta$-hydroxyvitamin D$_3$: UV $\lambda_{max}$=264, nm, $\epsilon$=18,000 mass spectrum, m/e: 401 (M$^+$, 15), 383 (20), 365 (5), 153 (100), 135 (80). [6-$^2$H]-1$\alpha$-hydroxy-5,6-trans-vitamin D$_3$: UV: $\lambda_{max}$ 270 nm; mass spectrum, m/e: 401 (M$^+$, 20), 383 (5), 153 (40), 135 (100). [6-$^2$H]-1$\beta$-hydroxy-5,6-trans-vitamin D$_3$: UV: $\lambda_{max}$ 269 nm; mass spectrum, m/e: 401 (M$^+$, 20), 383 (5), 153 (100), 135 (70).

Substitution of NaB$^3$H$_4$ as the reductant for NaB$^2$H$_4$ in a process similar to the above yields the corresponding 6-tritio-1-hydroxyvitamin D$_3$ isomers.

EXAMPLE 5

Preparation of [6-$^2$H]-24R,25-dihydroxyvitamin D$_3$ and [6-$^2$H]-24R,25-dihydroxy-5,6-trans-vitamin D$_3$.

(a) 24R,25-dihydroxy-6-oxo-3,5-cyclovitamin D$_3$

To 10 mg of 24R,25-dihydroxyvitamin D$_3$ in 500 $\mu$l of pyridine is added 5.0 mg of TsCl and the reaction is stirred at 10° overnight. At the end of this time it is poured over ice/H$_2$O, extracted with ether; the organic phase is washed with 1 N HCl, sat. NaHCO$_3$, H$_2$O, dried over MgSO$_4$ and chromatographed on 750$\mu$ silica gel tlc plate 1:1 ethyl acetate:hexane. The isolated 3$\beta$-tosyloxy-24R,25-dihydroxyvitamin D$_3$ (8 mg) is treated with t-butyldimethylsilylchloride in dimethylformamide/imidazole at 30°–40° overnight to protect the C-24 hydroxyl group. This crude material (7 mg) is solvolyzed in 5 ml of (9:1) acetone:H$_2$O containing 30 mg of NaHCO$_3$ as previously described in Example 1$\alpha$ to yield the corresponding 6-hydroxy-3,5-cyclovitamin intermediate which is directly oxidized in 2.0 ml of benzene and 30 mg of finely divided MnO$_2$. The reaction is heated to 60° for 6 hr. After the usual work-up and tlc purification 2.3 mg of 6-oxo-24R,25-dihydroxy- 3,5-cyclovitamin $D_3$ 24-silylether is obtained: UV: $\lambda_{max}=252$ nm; mass spectrum, m/e: 528 ($M^+$, 88) 471(M-57; 60), 469(M-59; 40), 121(53).

(b) 24R,25-dihydroxy-[6-$^2$H]-vitamin $D_3$ and 24R,25-dihydroxy-5,6trans-[6-$^2$H]-vitamin $D_3$ A solution of 2.0 mg of 6-oxo-24R,25-(OH)$_2$-3,5-cyclovitamin $D_3$ 24-silylether in 300 μl of ethanol is treated with 200 μl of a saturated solution of NaB$^2$H$_4$ in ethanol. After heating to 60° for 16 hr the reaction is quenched with H$_2$O for 15 min at room temp and extracted with ether. The dried organic extracts are concentrated in vacuo and treated with 0.5 ml of glacial acetic acid for 20 min at 55°. The cooled reaction is quenched with ice/sat NaHCO$_3$, extracted with ether; the organic extracts are washed with water, dried over MgSO$_4$ and concentrated in vacuo. The product is dissolved in ether and treated with 4% KOH in MeOH, room temperature, 1 hr, (to remove the acetyl group) and then treated with acetic acid/H$_2$O, tetrahydrofuran (3:1:1) at 55° for 24 hr (to remove the t-butyldimethylsilyl group) and the resulting cis and trans isomer mixture is separated on HPLC (8% 2-propanol/hexane 7.9 mm×30 cm μPorisil column) to yield [6-$^2$H]-24R,25-dihydroxy-5,6-trans-vitamin $D_3$: UV: $\lambda_{max}$ 271 nm; mass spectrum, m/e: 417 ($M^+$, 20), 399 (10), 137 (60), 119 (100), 59 (65), as the first eluating component (86 ml) and [6-$^2$H]-24R,25-dihydroxyvitamin $D_3$: UV: $\lambda_{max}$ 265 nm: mass spectrum, m/e: 417 ($M^+$, 15), 399 (10), 137 (60), 119 (90), 59 (50); nmr (δ): 0.56 (3H, s, 18—CH$_3$), 0.93 and 0.96 (3H, d, J=6.2 Hz, 21—CH$_3$), 1.17 (3H, s, 26—CH$_3$), 1.22 (3H, s, 27—CH$_3$), 3.34 (1H, m, 24—H), 3.95 (1H, m, 3α—H), 4.81 (1H, m (sharp), 19(Z)—H), 5.05 (1H, m (sharp), 19(E)—H), 6.01 (1H, s, 7—H) which elutes at 92 mls.

Utilizing a procedure similar to the above, but substituting 25,26-dihydroxyvitamin $D_3$ for 24,25-dihydroxyvitamin $D_3$ there is obtained 25,26-dihydroxy-[6-$^2$H]-vitamin $D_3$ and its 5,6-trans-isomer, and by the use of borotritide reductant in the same procedure the corresponding 6-tritio-24,25- and 25,26-dihydroxyvitamin D compounds are obtained.

EXAMPLE 6

Preparation of 1α-Hydroxy-[6-$^2$H]-vitamin $D_2$ and 1α-hydroxy-5,6-trans[6-$^2$H]-vitamin $D_2$ and the corresponding 1β-hydroxy-isomers.

(a) 1α-Hydroxy-6-oxo-3,5-cyclovitamin $D_2$ and derivatives.

A sample of 6-oxo-3,5-cyclovitamin $D_2$ (20 mg) obtained as described in Example 2b is subjected to allylic oxidation with selenium dioxide/t-butyl hydroperoxide using the condition described in Example 4a to yield a mixture from which 1α-hydroxy-6-oxo-3,5-cyclovitamin $D_2$ (4 mg) is isolated and purified by high pressure liquid chromatography, yielding material with the following spectral properties: UV, $\lambda_{max}$ 252 nm, (ε=12,000); mass spectrum, m/e 410 ($M^+$), 285, 267, 151, 135, 133; nmr (δ) 4.30 (1H, m, 1β—H).

Treatment of this 1α-hydroxylated product with bis-trimethylsilyltrifluoroacetamide in pyridine for 3 hr gives the corresponding 1α-O-trimethylsilyl derivative (m/e 482, $M^+$). The corresponding 1α-O-t-butyldimethylsilyl derivative is prepared by treating 1α-hydroxy-6oxo-3,5-cyclovitamin $D_2$ with t-butyldimethylsilyl chloride in imidazole/dimethylformamide at 40° overnight [mass spectrum, m/e 524 ($M^+$), 467 ($M^+$-57)]. Treatment of the 1α-hydroxy compound with acetic anhydride in pyridine for 3 hr gives 1α-acetoxy-6-oxo-3,5-cyclovitamin $D_2$: UV, $\lambda_{max}$ 252 nm; mass spectrum, m/e 452 ($M^+$), 392 (M-60).

(b) 1α-Hydroxy-[6-$^2$H]-vitamin $D_2$ and 1α-hydroxy-5,6-trans-[6-$^2$H]vitamin $D_2$.

1α-Acetoxy-6-oxo-3,5-cyclovitamin $D_2$ (3.5 mg) is reduced with excess sodium borodeuteride (NaB$^2$H$_4$) exactly as described in Example 1c to yield 1α-acetoxy-6-hydroxy-3,5-cyclo-[6-$^2$H]vitamin $D_2$ which is directly subjected to solvolysis, by dissolution in 0.4 ml of dioxane/H$_2$O (3:1), warming to 55° C., and addition of 10 μl of an aqueous solution of p-toluenesulfonic acid (50 μg/μl) after which heating is continued for 10 min. The reaction is quenched by addition of saturated NaHCO$_3$ solution, and extracted with two portions of ether. The ether phase is washed with sat. NaHCO$_3$, water, dried over MgSO$_4$ and the solvent is removed. Preparative thin layer chromatography (silica gel, hexane:ethyl acetate, 8:2) yields 1.5 mg of 1α-acetoxy-[6-$^2$H]-vitamin $D_2$ [UV, $\lambda_{max}$ 265 nm; mass spectrum, m/e 455 ($M^+$)] and 0.5 mg of 1α-acetoxy-5,6-trans[6-$^2$H]-vitamin $D_2$ [UV, $\lambda_{max}$ 273 nm; mass spectrum, m/e 455 ($M^+$)].

The acetyl groups are removed by treating each compound with a solution of LiAlH$_4$ in ether (20 min, room temp.). This gives, from the cis-acetate, after the standard workup, 1.2 mg of 1α-hydroxy-[6-$^2$H]vitamin $D_2$: UV, $\lambda_{max}$ 265 nm; mass spectrum, m/e 413 ($M^+$), 395, 377, 288, 270, 252, 153, and 135 (base peak) and nmr (δ) 0.56 (3H, s, 18—H$_3$), 5.00 and 5.32 (19 (Z and E)—H), 5.20 (2H, m, 22 and 23—H), 6.00 (1H, s, 7—H), 4.20 and 4.40 (C-3 and C-1—H), which is chromatographically identical with authentic unlabeled 1α-hydroxyvitamin $D_2$. Similar reduction of the trans-acetate given 1α-hydroxy-5,6-trans-[6-$^2$H]-vitamin $D_2$; UV, $\lambda_{max}$ 272, nm; mass spectrum, m/e 413 ($M^+$), 395, 377, 288, 270, 252, 153 and 125 (base) which is chromatographically identical with authentic unlabeled 1α-hydroxy-5,6-trans-vitamin $D_2$.

(c) 1α- and 1β-hydroxy-6-oxo-3,5-cyclovitamin $D_2$ and conversion to [6-$^2$H]-vitamin $D_2$ products.

6-oxo-3,5-cyclovitamin $D_2$ (10 mg) prepared as described in Example 2b, is oxidized with selenium dioxide/t-butyl hydroperoxide exactly as described in Example 4a to yield after purification as in Example 4a, a mixture (ca. 2:1) of 1β-hydroxy-6-oxo-3,5-cyclovitamin $D_2$ and 1α-hydroxy-6-oxo-3,5-cyclovitamin $D_2$, exhibiting the following spectral properties: UV, $\lambda_{max}$ 252 nm; mass spectrum, m/e 410 ($M^+$), 285, 151, 135; nmr, (δ) 4.30 (1H, m, 1β—H) 4.60 (1H, m, 1α—H).

Reduction of this product with sodium borodeuteride (NaB$^2$H$_4$) followed by acetic acid solvolysis and separation of products exactly as described in Example 4b gives four labeled products, namely, 1βhydroxy-[6-$^2$H]-vitamin $D_2$ 3-acetate, 1α-hydroxy-[6-$^2$H]-vitamin $D_2$ 3-acetate, 1β-hydroxy-5,6-trans-[6-$^2$H]-vitamin $D_2$ 3-acetate, and 1α-hydroxy-5,6-trans-[6-$^2$H]-vitamin $D_2$ 3-acetate.

Removal of the acetyl groups from each of the products by reduction as described in Example 4c gives 1α-hydroxy-[6-$^2$H]-vitamin $D_2$ and its 5,6-trans-isomer, identical to the products described in Example 6b above, as well as 1β-hydroxy-[6-$^2$H]-vitamin $D_2$ and its 5,6-transisomer.

EXAMPLE 7

Preparation of 1α,25-Dihydroxy-[6-³H]-vitamin D₃ and 1α,25-Dihydroxy5,6-trans-[6-³H]-vitamin D₃.

(a) 1α,25-dihydroxy-6-oxo-3,5-cyclovitamin D₃ and 1-acetate.

Oxidation of 25-hydroxy-6-oxo-3,5-cyclovitamin D₃ (Example 3b) with selenium dioxide and t-butyl hydroperoxide, using the conditions described in Example 4a, yields (ca. 60–70%) a mixture of the desired 1α- and 1β-hydroxy-derivatives. This mixture is directly acetylated by treatment with excess acetic anhydride in pyridine at room temperature for 2 hours, and the resulting mixture of 1α- and 1β-acetates is separated on high pressure liquid chromatography (hplc) using a silica gel column (μ-Porisil, 0.79×30 cm) and 1.5% 2-propanol in hexane as eluting solvent. This provides 1β-acetoxy-25-hydroxy-6-oxo-3,5-cyclovitamin D₃ as the first eluting compound [mass spectrum, m/e 456 (M⁺, 100%), 438 (48), 396 (57), 267 (18), 245 (45), 173 (35) 151 (55), 135 (50) 133 (75)], followed by 1α-acetoxy-25-hydroxy-6-oxo-3,5-cyclovitamin D₃ [mass spectrum, m/e 456 (M⁺, 60), 438 (25) 396 (55), 267 (18), 245 (33), 173 (30), 151 (35), 135 (40), 131 (75). Hydrolysis of the 1α-acetoxy compound (10% KOH/MeOH, 40°–50°, 2 hr) gives 1α,25-dihydroxy6-oxo-3,5-cyclovitamin D₃: UV, λ$_{max}$ 252 nm; mass spectrum, m/e 414 (M⁺) 285, 267, 151, 135, 133; nmr (δ) 4.30 (1H, m, 1β—H).

(b) 1α,25-dihydroxy-[6-³H]-vitamin D₃ and 1α,25-dihydroxy-5,6-trans-[6-³H]-vitamin D₃.

Reduction of 1 mg of 1α,25-dihydroxy-6-oxo-3,5-cyclovitamin D₃ with sodium borotritide [NaB³H₄, 48 Ci/mmole] following the procedure of Example 2c gives the desired 6-trito-6-hydroxy-intermediate which is immediately solvolyzed in warm glacial acetic acid according to the procedure of Example 2c to give after workup a mixture of 1α,25-dihydroxy[6-³H]vitamin D₃ 3-acetate and its 5,6-trans isomer. These products are separated by high pressure liquid chromatography (silica gel column, 0.6×25 cm Zorbax-SIL) using 5% 2-propanol/hexane as eluting solvent and the products are individually deacetylated by reduction with excess LiAlH₄ (in ether, 20 min, room temp.). This gives 1α,2-5dihydroxy-[6-³H]-vitamin D₃ (0.35 mg) with a specific activity of 12 Ci/mmole which shows UV, λ$_{max}$ 265 nm and co-chromatographs on high pressure liquid chromatography and thin layer chromatography with authentic unlabeled 1α,25-dihydroxyvitamin D₃. Similar reduction of the 5,6-trans-3-acetate yields 1α,25-dihydroxy-5,6-trans-[6-³H]-vitamin D₃ (0.1 mg, 12 Ci/mmole) UV, λ$_{max}$ 272 nm, which co-chromatographs in all systems with authentic 1α,25-dihydroxy-5,6-trans-vitamin D₃.

Utilizing procedures similar to that described above, but substituting 25-hydroxy-6-oxo-3,5-cyclovitamin D₂ (Example 3), 6-oxo-26,27dinor-3,5-cyclo-vitamin D₃-25-carboxylic acid ester (Example 3) or 24,25-dihydroxy-6-oxo-3,5-cyclo-vitamin D₃ (Example 5) or 25,26-dihydroxy-6-oxo-3,5-cyclovitamin D₃ for 25-hydroxy-6-oxo-3,5-cyclovitamin D₃ there is obtained 1α,25-dihydroxy-[6-³H]-vitamin D₂, 1α-hydroxy-[6-³H]-26,27-dinorvitamin D₃-25-carboxylic acid ester, 1α,24,25-trihydroxy-[6-³H]-vitamin D₃ and 1α,25,26-trihydroxy-[6-³H]vitamin D₃, respectively, and the corresponding 5,6-trans-isomers.

Having thus described the invention, what is claimed is:

1. A method for preparing vitamin D- and 5,6-trans vitamin D-compounds which are isotopically labeled at carbon 6 of the molecule with deuterium or tritium which comprises, reducing, a compound having the general formula

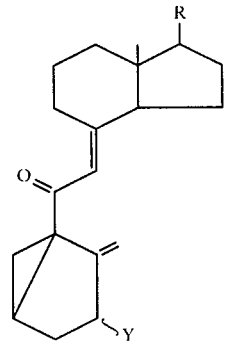

where R represents the sidechain as desired in the labeled product and Y is hydrogen, hydroxy or protected-hydroxy with a tritio-or deutero-borohydride reducing reagent, whereby the corresponding 6-deutero- or 6-tritio-substituted-6-hydroxy product is obtained subjecting said reduction product to acid catalyzed solvolysis, whereby the 6-deutero- or 6-tritio-vitamin D and 5,6-trans vitamin D compound is obtained, and recovering the desired labeled product.

2. The process of claim 1, wherein any hydroxy-protecting groups are removed by hydrolysis or hydride reduction, after the solvolysis step or after the recovery of the desired labeled product.

3. The process of claim 1 in which Y is hydroxy or protected-hydroxy.

4. The process of claim 3 wherein the 6-oxo-3,5-cyclovitamin D compound subjected to reduction is prepared by allylic oxidation of the corresponding 1-deoxy-6-oxo-3,5-cyclovitamin D compound in the presence of selenium dioxide and a hydroperoxide.

5. The process of claims 1 or 3 wherein the solvolysis is conducted in the presence of acetic or formic acid.

6. The process of claims 1 or 3 wherein the solvolysis is conducted in the presence of toluenesulfonic acid.

7. Compounds having the formula

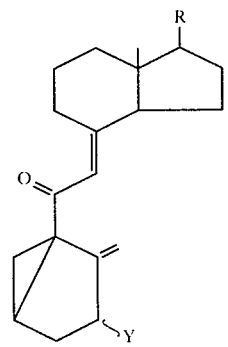

wherein Y is hydrogen, hydroxy or protected-hydroxy, and R is selected from the group consisting of hydrogen, alkyl

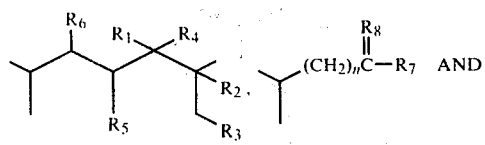

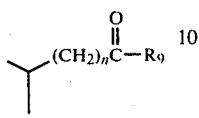

wherein each of $R_1$, $R_2$ and $R_3$ is selected from the group consisting of hydrogen, hydroxy, protected-hydroxy, alkyl and fluoro, and where $R_1$ and $R_2$ or $R_2$ and $R_3$, when taken together, form an epoxide, acetonide, or cyclic-O-boronate grouping, $R_4$ is hydrogen or alkyl, $R_5$ and $R_6$ are hydrogen or, when taken together, form a double bond, except that $R_1$, $R_2$, $R_3$, $R_4$, $R_5$ and $R_6$ may not all be hydrogen when Y is hydrogen, $R_7$ is selected from the group consisting of hydrogen and alkyl, $R_8$ represents a carbonyl or protected-carbonyl group, $R_9$ is selected from the group consisting of hydroxy and O-alkyl, and n is 1, 2 or 3.

8. Compounds of claim 7 having the formula

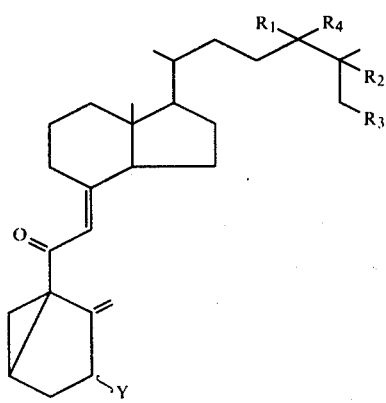

where Y is hydrogen, hydroxy or protected-hydroxy, $R_1$, $R_2$ and $R_3$ are each selected from the group consisting of hydrogen, hydroxy, protected-hydroxy, alkyl and fluoro and $R_4$ is hydrogen or alkyl, and where $R_1$ and $R_2$ or $R_2$ and $R_3$, when taken together, form an epoxide, acetonide or cyclic-O-boronate grouping, except that Y, $R_1$, $R_2$, $R_3$ and $R_4$ may not all be hydrogen.

9. Compounds of claim 7 having the formula

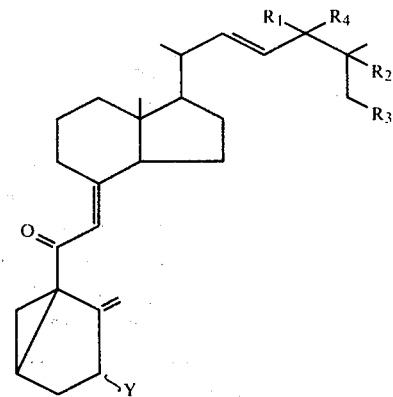

where Y is hydrogen, hydroxy or protected-hydroxy, $R_1$, $R_2$ and $R_3$ are each selected from the group consisting of hydrogen, hydroxy, protected-hydroxy, alkyl, and fluoro and $R_4$ is hydrogen or alkyl, and where $R_1$ and $R_2$ or $R_2$ and $R_3$, when taken together, form an epoxide, acetonide or cyclic-O-boronate group.

10. Compounds of claim 7 wherein R is selected from the group consisting of

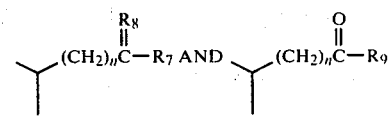

wherein $R_7$ is selected from the group consisting of hydrogen and alkyl, $R_8$ represents a carbonyl or protected-carbonyl group, $R_9$ is selected from the group consisting of hydroxy and O-alkyl, and n is 1, 2 or 3.

11. 25-hydroxy-6-oxo-3,5cyclovitamin $D_3$.

12. The 25-O-acyl and 25-O-alkylsilyl derivatives of the compound of claim 11.

13. 1-hydroxy-6-oxo-3,5-cyclovitamin $D_3$.

14. The 1-O-acyl and 1-O-alkylsilyl derivatives of the compound of claim 13.

15. 1,25-dihydroxy-6-oxo-3,5-cyclovitamin $D_3$.

16. Compounds according to claim 15 wherein at least one of the hydroxy groups is protected by a group consisting of acyl or alkylsilyl.

17. Compounds having the formula

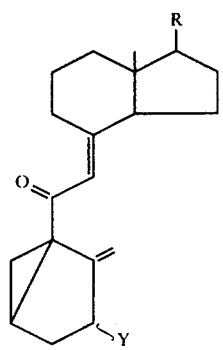

wherein Y is selected from the group consisting of hydrogen, hydroxy and protected hydroxy, and wherein R is selected from the group consisting of

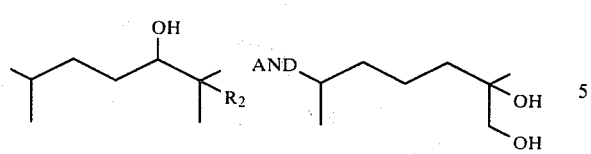

wherein R$_2$ is selected from the group consisting of hydrogen, hydroxy, O-acyl and O-alkylsilyl.

18. The compounds of claim 17 wherein Y is hydrogen or hydroxy and wherein R$_2$ is hydroxy.

19. The compounds of claim 17 or 18 wherein the 24-hydroxy group or the 26-hydroxy group is protected by acyl or alkylsilyl groups.

20. 6-oxo-3,5-cyclovitamin D$_2$.

21. 25-hydroxy-6-oxo-3,5-cyclovitamin D$_2$

22. The 25-O-acyl and 25-O-alkylsilyl derivatives of the compound of claim 21.

23. 1-hydroxy-6-oxo-3,5-cyclovitamin D$_2$.

24. The 1-O-acyl and 1-O-alkylsilyl derivatives of the compound of claim 23.

25. 1,25-dihydroxy-6-oxo-3,5-cyclovitamin D$_2$.

26. The compounds of claim 25 wherein one or none of the hydroxy groups is protected by acyl or alkylsilyl groups.

27. Compounds having the formula

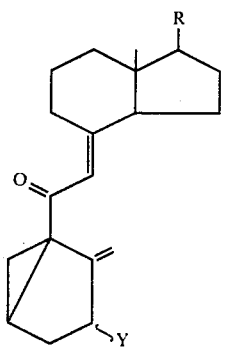

where Y is selected from the group consisting of hydrogen, hydroxy and protected-hydroxy, and
R is selected from the group consisting of

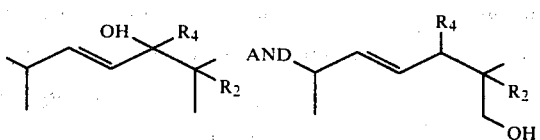

wherein R$_2$ is selected from the group consisting of hydrogen, hydroxy, O-acyl and O-alkylsilyl, and wherein R$_4$ is hydrogen or methyl.

28. The compounds of claim 27 wherein Y is hydrogen or hydroxy, R$_2$ is hydroxy, and R$_3$ is methyl.

* * * * *

UNITED STATES PATENT OFFICE
CERTIFICATE OF CORRECTION

Patent No. 4,297,289      Dated October 27, 1981

Inventor(s) DeLuca et al

It is certified that error appears in the above-identified patent and that said Letters Patent are hereby corrected as shown below:

Column 23, the schematic -

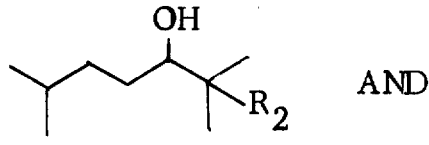 AND 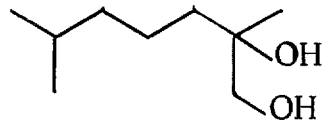

should be -

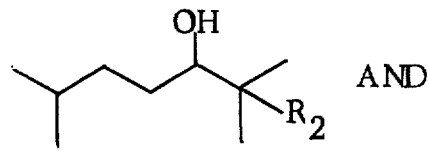 AND 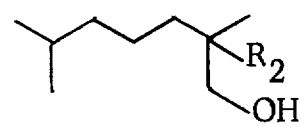

Signed and Sealed this

Twenty-third Day of February 1982

[SEAL]

Attest:

GERALD J. MOSSINGHOFF

Attesting Officer      Commissioner of Patents and Trademarks